(12) United States Patent
Simcock et al.

(10) Patent No.: US 10,379,036 B2
(45) Date of Patent: Aug. 13, 2019

(54) INTEGRATED COMPUTATIONAL ELEMENT DESIGNED FOR MULTI-CHARACTERISTIC DETECTION

(71) Applicant: Halliburton Energy Services, Inc., Houston, TX (US)

(72) Inventors: Michael N. Simcock, Columbia, SC (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 328 days.

(21) Appl. No.: 14/888,198

(22) PCT Filed: Feb. 19, 2014

(86) PCT No.: PCT/US2014/017178
§ 371 (c)(1),
(2) Date: Oct. 30, 2015

(87) PCT Pub. No.: WO2015/126386
PCT Pub. Date: Aug. 27, 2015

(65) Prior Publication Data
US 2016/0299059 A1    Oct. 13, 2016

(51) Int. Cl.
| | |
|---|---|
| G01N 21/31 | (2006.01) |
| G01J 3/28 | (2006.01) |
| G06E 3/00 | (2006.01) |
| G01J 3/10 | (2006.01) |
| G06F 17/50 | (2006.01) |
| G01J 3/12 | (2006.01) |

(52) U.S. Cl.
CPC ............ *G01N 21/31* (2013.01); *G01J 3/10* (2013.01); *G01J 3/28* (2013.01); *G06E 3/001* (2013.01); *G06F 17/50* (2013.01); *G01J 2003/1226* (2013.01)

(58) Field of Classification Search
CPC .. G01N 21/31; G06F 17/50; G01J 3/28; G01J 3/10; A61K 2300/00; A61K 31/57; A61K 31/185; A61K 31/335
See application file for complete search history.

(56) References Cited

U.S. PATENT DOCUMENTS

| | | | |
|---|---|---|---|
| 5,004,904 A | 4/1991 | Yamakawa et al. | |
| 5,612,782 A * | 3/1997 | Keranen | G01D 18/00 250/252.1 |
| 6,176,323 B1 * | 1/2001 | Weirich | E21B 21/08 175/40 |
| 6,549,861 B1 * | 4/2003 | Mark | G01J 3/28 356/931 |
| 6,684,099 B2 | 1/2004 | Ridder et al. | |
| 6,864,331 B1 * | 3/2005 | Reimers | B01J 19/0006 356/319 |
| 8,237,920 B2 | 8/2012 | Jones et al. | |

(Continued)

OTHER PUBLICATIONS http://www.thefreedictionary.com/correspond.*

(Continued)

*Primary Examiner* — Mohamed K Amara
(74) *Attorney, Agent, or Firm* — Haynes and Boone, LLP

(57) ABSTRACT

A single Integrated Computational Element ("ICE") predictive of multiple sample characteristics.

26 Claims, 4 Drawing Sheets

(56) References Cited

U.S. PATENT DOCUMENTS

| | | | | |
|---|---|---|---|---|
| 8,352,205 B2* | 1/2013 | Myrick | ................... | G01J 3/02 |
| | | | | 250/252.1 |
| 8,575,541 B1* | 11/2013 | Jamison | ................ | G01N 21/85 |
| | | | | 250/253 |
| 8,885,163 B2* | 11/2014 | Morys | ................... | G01N 21/31 |
| | | | | 250/339.11 |
| 8,908,165 B2* | 12/2014 | Tunheim | ............... | G01N 21/85 |
| | | | | 356/73 |
| 9,041,932 B2* | 5/2015 | Priore | ................. | G01N 21/255 |
| | | | | 356/301 |
| 9,097,649 B2* | 8/2015 | Simcock | ............... | G02B 5/285 |
| 9,157,800 B2* | 10/2015 | Priore | ..................... | G01J 3/32 |
| 9,329,086 B2* | 5/2016 | Treado | ..................... | G01J 3/51 |
| 9,890,634 B2* | 2/2018 | Mitchell | ............... | E21B 47/102 |
| 10,031,074 B2* | 7/2018 | Gao | ..................... | G01N 21/274 |
| 10,175,109 B2* | 1/2019 | Perkins | ................. | G01N 21/31 |
| 2002/0059047 A1* | 5/2002 | Haaland | .................... | G01J 3/28 |
| | | | | 703/2 |
| 2002/0154315 A1* | 10/2002 | Myrick | ................... | G01J 3/18 |
| | | | | 356/305 |
| 2002/0193671 A1* | 12/2002 | Ciurczak | ........... | A61B 5/14532 |
| | | | | 600/316 |
| 2006/0197015 A1* | 9/2006 | Sterling | ............ | A61B 5/14532 |
| | | | | 250/252.1 |
| 2007/0291251 A1 | 12/2007 | Rensen et al. | | |
| 2008/0112853 A1* | 5/2008 | Hall | .................... | A61B 5/1495 |
| | | | | 422/82.05 |
| 2009/0015819 A1* | 1/2009 | Van Beek | ................ | G01J 3/28 |
| | | | | 356/39 |
| 2009/0150106 A1* | 6/2009 | Erickson | ............... | G01N 21/05 |
| | | | | 702/85 |
| 2009/0316150 A1* | 12/2009 | Myrick | .................... | G01J 3/02 |
| | | | | 356/326 |
| 2012/0150451 A1* | 6/2012 | Skinner | .............. | G01N 33/2823 |
| | | | | 702/24 |
| 2013/0284894 A1 | 10/2013 | Freese et al. | | |
| 2014/0076551 A1* | 3/2014 | Pelletier | ................ | G01N 21/47 |
| | | | | 166/253.1 |
| 2015/0346087 A1* | 12/2015 | Skinner | .................. | G01N 21/31 |
| | | | | 250/206 |
| 2016/0091478 A1* | 3/2016 | Pearl, Jr. | .................. | C09K 8/42 |
| | | | | 250/206 |
| 2016/0186558 A1* | 6/2016 | Freese | .................... | E21B 49/08 |
| | | | | 250/255 |
| 2016/0209323 A1* | 7/2016 | Pelletier | ................ | G01N 21/31 |
| 2016/0266033 A1* | 9/2016 | Simcock | .............. | G01N 21/255 |
| 2016/0282262 A1* | 9/2016 | Skinner | .................. | G01N 21/31 |

OTHER PUBLICATIONS http://www.thefreedictionary.com/makeup.*

International Search Report and The Written Opinion of the International Searching Authority, or the Declaration, dated May 19, 2014, PCT/US2014/016102, 13 pages, ISA/US.

Jones, et al, "Field Test of the Integrated Computational Elements: A New Optical Sensor for Downhole Fluid Analysis," SPWLA 54th Annual Logging Symposium, Jun. 22-26, 2013.

Soyemi, et al, "Design and Testing of a Multivariate Optical Element: The First Demonstration of Multivariate Optical Computing for Predictive Spectroscopy," Analytical Chemistry, Mar. 15, 2001, vol. 73, No. 6, pp. 1069-1079.

* cited by examiner

INTEGRATED COMPUTATIONAL ELEMENT DESIGNED FOR MULTI-CHARACTERISTIC DETECTION

The present application is a U.S. National Stage patent application of International Patent Application No. PCT/US2014/017178, filed on Feb. 19, 2014, the benefit of which is claimed and the disclosure of which is incorporated herein by reference in its entirety.

FIELD OF THE DISCLOSURE

Embodiments of present disclosure generally relate to optical computing and, more particularly, to multivariate optical computing devices that utilize an Integrated Computational Element ("ICE") designed to detect multiple sample characteristics.

BACKGROUND

In recent years, optical computing techniques have been developed for applications in the oil and gas industry in the form of optical sensors on downhole or surface equipment to evaluate a variety of fluid properties. In general, optical computing devices, also commonly referred to as "opticoanalytical devices," can be used to analyze and monitor a sample substance in real time. Such optical computing devices will often employ a light source that emits electromagnetic radiation that either reflects from or is transmitted through the sample and optically interacts with an optical processing element to determine quantitative and/or qualitative values of one or more physical or chemical properties of the substance being analyzed. The optical processing element may be, for example, an ICE. One type of an ICE is an optical thin film interference device, also known as a multivariate optical element ("MOE"). Each ICE can be designed to operate over a continuum of wavelengths in the electromagnetic spectrum from the UV to mid-infrared (MIR) ranges, or any sub-set of that region. Electromagnetic radiation that optically interacts with the sample substance is changed and processed by the ICE so as to be measured by a detector. The output of the detector is then correlated to a physical or chemical property of the substance being monitored.

Fundamentally, optical computing devices utilize optical elements to perform calculations, as opposed to the hardwired circuits of conventional electronic processors. When light from a light source interacts with a substance, unique physical and chemical information about the substance is encoded in the electromagnetic radiation that is reflected from, transmitted through, or radiated from the sample. Thus, the optical computing device, through use of the ICE and one or more detectors, is capable of extracting the information of one or multiple characteristics/analytes within a substance and converting that information into a detectable output signal reflecting the overall properties of a sample. Such characteristics may include, for example, the presence of certain elements, compositions, fluid phases, etc. existing within the substance.

Currently, ICEs are assessed by applying an ICE regression vector to a single set of calibration data (i.e., spectral data set) to evaluate a performance factor such as, for example, standard error of calibration ("SEC"). This procedure is performed on a set of spectral data that describes a single chemical system that contains one or more components: its target characteristic/analyte and the remaining components (including spectral interferents), usually referred to the matrix. A subset of the chemical system can be used for validation purposes to calculate the standard error of prediction ("SEP"); this subset represents the same chemical system and the calibration set. An illustrative ICE (e.g., MOE), which may consist of a series of alternating layers of high and low refractive index materials deposited onto an optical substrate which has a transmission function (T), is designed by assessing the performance factor, for example SEC, and using a minimization function to adjust the layers to make an ICE with a low SEC, which is thus as predictive as possible. Accordingly, the ICE is predictive for only one sample characteristic.

In some cases, measurements of more than one characteristic of a substance are needed. This is accomplished by either multiple optical computing systems (each with its own ICE), or a single larger optical computing system with a plurality of ICEs (each measuring a single characteristic separately). However, is some cases (like downhole reservoir fluid characterization), there are space and size requirements that prohibit multiple or large optical computing systems. Accordingly, there is a need in the art for an ICE which is predictive for multiple sample characteristics, thereby minimizing the number of ICEs required to measure the plurality of characteristics.

DESCRIPTION OF ILLUSTRATIVE EMBODIMENTS

Figure 1:
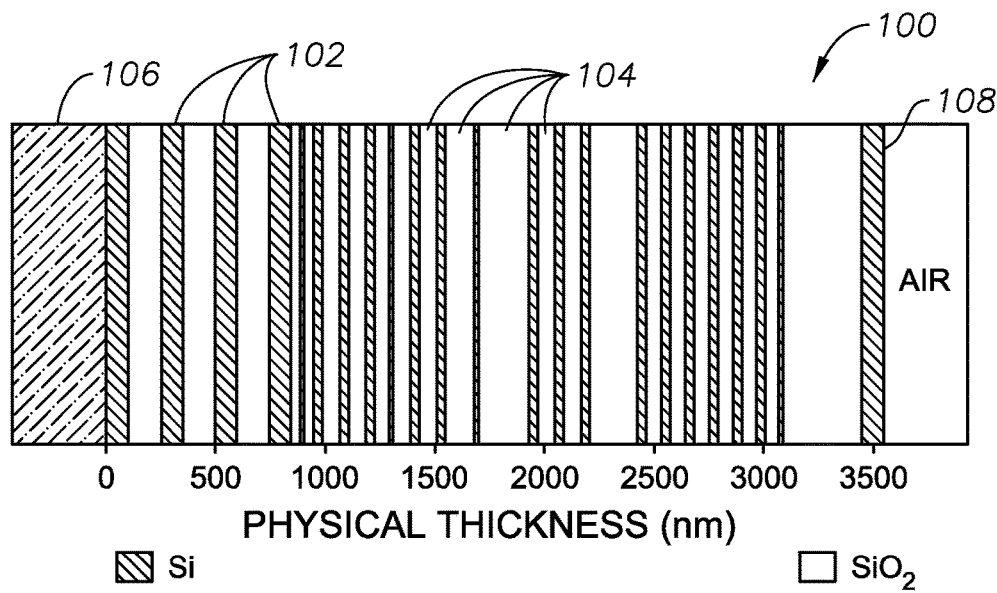
FIG. 1 illustrates a multi-characteristic ICE fabricated in accordance to illustrative methods of the present disclosure.

Illustrative embodiments and related methods of the present disclosure are described below as they might be employed in an ICE that is predictive for multiple characteristics. In the interest of clarity, not all features of an actual implementation or method are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methods of the disclosure will become apparent from consideration of the following description and drawings.

As described herein, the present disclosure is directed to an optical computing device having at least one ICE that detects multiple characteristics of a substance. To design such an ICE for multi-analytic purposes, a single ICE regression vector is applied to multiple calibration spectra data sets that represent multiple chemical systems. Thereafter, the performance factor of the ICE design (e.g., its SEC, SEP, sensitivity, S/N, % transmission, etc.) is quantified and utilized to adjust ICE layer thicknesses to thereby optimize the performance factor of the ICE design considering each of the calibration data sets. Accordingly, an ICE fabricated using the design will be predictive for multiple characteristics which were present in the chemical systems used during the design phase.

The optical computing devices described herein may be used in the oil and gas industry, such as for monitoring and detecting oil/gas-related substances (e.g., hydrocarbons, cements, drilling fluids, completion fluids, treatment fluids, etc.). It will be appreciated, however, that the optical computing devices described herein may equally be used in other technology fields including, but not limited to, the food industry, the paint industry, the mining industry, the agricultural industry, the medical and pharmaceutical industries, the automotive industry, the cosmetics industry, water treatment facilities, and any other field where it may be desired to monitor substances in real time.

As used herein, the term "substance," "sample" or variations thereof, refers to at least a portion of matter or material of interest to be tested or otherwise evaluated with the help of the optical computing devices described herein. The substance may be any fluid capable of flowing, including particulate solids, liquids, gases (e.g., air, nitrogen, carbon dioxide, argon, helium, methane, ethane, butane, and other hydrocarbon gases, hydrogen sulfide, and combinations thereof), slurries, emulsions, powders (e.g., cements, concretes, etc.), drilling fluids (i.e., "muds"), glasses, mixtures, combinations thereof. The substance may include, but is not limited to, aqueous fluids (e.g., water, brines, etc.), non-aqueous fluids (e.g., organic compounds, hydrocarbons, oil, a refined component of oil, petrochemical products, and the like), acids, surfactants, biocides, bleaches, corrosion inhibitors, foamers and foaming agents, breakers, scavengers, stabilizers, clarifiers, detergents, treatment fluids, fracturing fluids, formation fluids, or any oilfield fluid, chemical, or substance commonly found in the oil and gas industry. The substance may also refer to solid materials such as, but not limited to, rock formations, concrete, solid wellbore surfaces, pipes or flow lines, and solid surfaces of any wellbore tool or projectile (e.g., balls, darts, plugs, etc.).

As used herein, the term "characteristic" or "characteristic of interest" refers to a chemical, mechanical, or physical property of a substance or a sample of the substance. The characteristic of the substance may include a quantitative or qualitative value of one or more chemical constituents or compounds present therein or any physical property associated therewith. Such chemical constituents and compounds may be referred to herein as "analytes." Illustrative characteristics of a substance that can be analyzed with the help of the optical processing elements described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, transmittance, state of matter (solid, liquid, gas, emulsion, mixtures thereof, etc.), and the like.

As used herein, the term "electromagnetic radiation" refers to radio waves, microwave radiation, terahertz, infrared and near-infrared radiation, visible light, fluorescent light, ultraviolet light, X-ray radiation and gamma ray radiation.

As used herein, the phrase "optically interact" or variations thereof refers to the reflection, transmission, scattering, diffraction, or absorption of electromagnetic radiation either on, through, or from an optical processing element (e.g., an integrated computational element) or a substance being analyzed with the optical computing device. Accordingly, optically interacted light refers to electromagnetic radiation that has been reflected, transmitted, scattered, diffracted, or absorbed by, emitted, or re-radiated, for example, using an optical processing element, but may also apply to optical interaction with a substance.

As used herein, the term "optical computing device" refers to an optical device that is configured to receive an input of electromagnetic radiation associated with a substance and produce an output of electromagnetic radiation from an optical processing element arranged within or otherwise associated with the optical computing device. The optical processing element may be, for example, an ICE. The electromagnetic radiation that optically interacts with the optical processing element is changed so as to be readable by a detector, such that an output of the detector can be correlated to a particular characteristic of the substance being analyzed. The output of electromagnetic radiation from the optical processing element can be reflected, transmitted, and/or dispersed electromagnetic radiation. Whether the detector analyzes reflected, transmitted, or dispersed electromagnetic radiation may be dictated by the structural parameters of the optical computing device as well as other considerations known to those skilled in the art.

Referring to FIG. 1, illustrated is an illustrative ICE 100 which may be fabricated through utilization of the illustrative design processes described herein. ICE 100 may include a plurality of alternating layers 102 and 104, such as, for example, silicon (Si) and quartz ($SiO_2$), respectively. Other non-limiting examples of layer material include niobium, germanium and Germania, MgF, SiO, and other high and low index materials, although persons of ordinary skill in the art having the benefit of this disclosure will understand that these layers consist of materials whose index of refraction is high and low, respectively. The layers 102, 104 may be strategically deposited on an optical substrate 106. In some embodiments, the optical substrate 106 is BK-7 optical glass. In other embodiments, the optical substrate 106 may be other types of optical substrates, such as quartz, sapphire, silicon, germanium, zinc selenide, zinc sulfide, or various plastics such as polycarbonate, polymethalmethacrylate PMMA), polyvinylchloride (PVC), diamond, ceramics, etc., as known in the art. At the opposite end (e.g., opposite the optical substrate 106), the ICE 100 may include a layer 108 that is generally exposed to the environment of the device or installation. The number of layers 102, 104 and the thickness of each layer 102, 104 may be determined from the spectral attributes acquired from a spectroscopic analysis of a characteristic of the sample using a conventional spectroscopic instrument.

The spectrum of interest of a given characteristic of a sample typically includes any number of different wavelengths. It should be understood that the illustrative ICE 100 in FIG. 1 does not in fact represent any particular characteristic of a given sample, but is provided for purposes of illustration only. Consequently, the number of layers 102, 104 and their relative thicknesses, as shown in FIG. 1, bear no correlation to any particular characteristic of a given sample. Nor are the layers 102, 104 and their relative thicknesses necessarily drawn to scale, and therefore should not be considered to limit the present disclosure. Moreover, those skilled in the art will readily recognize that the materials that make up each layer 102, 104 may vary, depending on the application, cost of materials, and/or applicability of the material to the sample substance. For example, the layers 102, 104 may be made of, but are not limited to, silicon, quartz, germanium, water, combinations thereof, or other materials of interest.

The multiple layers 102, 104 exhibit different complex refractive indices. By properly selecting the materials of the layers 102, 104 and their relative thicknesses and spacing, the illustrative ICE 100 may be configured to selectively pass/reflect/refract predetermined fractions of light (i.e., electromagnetic radiation) at different wavelengths. Through the use of regression techniques, the corresponding output light intensity of the ICE 100 conveys information regarding a sample characteristic of interest. Accordingly, selection of layer thickness and spacing are critically important to the ICE design process.

Figure 2:
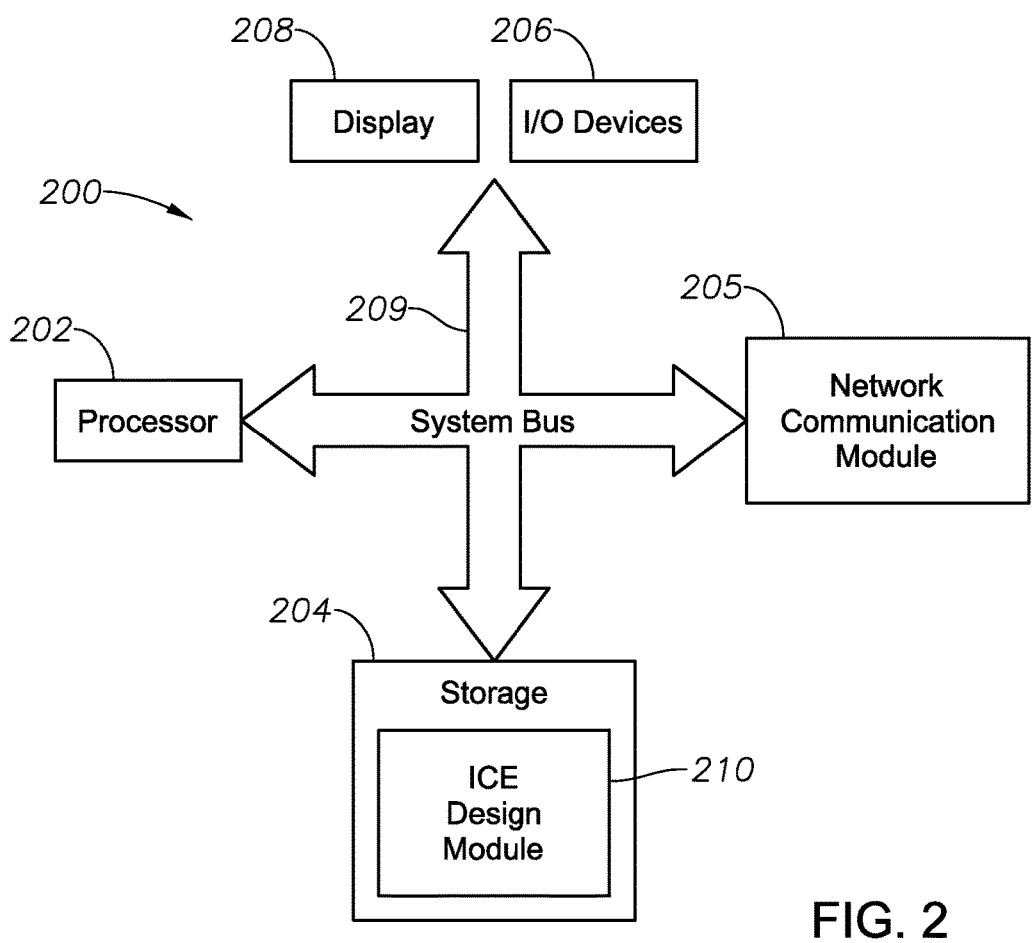
FIG. 2 is a block diagram of an ICE design system in accordance to an illustrative embodiment of the present disclosure.

In view of the foregoing, FIG. 2 shows a block diagram of an ICE design system according to an illustrative embodiment of the present disclosure. As will be described herein, ICE design system 200 provides a platform for ICE design optimization and analysis to facilitate the design of an ICE that is predictive for multiple characteristics. Illustrative embodiments of ICE design system 200 described herein enables a single ICE to be designed for multiple analytical purposes by applying the single ICE regression vector to calibration spectra representing two or more chemical systems.

Referring to FIG. 2, ICE design system 200 includes at least one processor 202, a non-transitory, computer-readable storage 204, transceiver/network communication module 205, optional I/O devices 206, and an optional display 208 (e.g., user interface), all interconnected via a system bus 209. In one embodiment, the network communication module 205 is a network interface card (NIC) and communicates using the Ethernet protocol. In other embodiment, the network communication module 105 may be another type of communication interface such as a fiber optic interface and may communicate using a number of different communication protocols. Software instructions executable by the processor 202 for implementing software instructions stored within ICE design module 210 in accordance with the illustrative embodiments described herein, may be stored in storage 204 or some other computer-readable medium.

Although not explicitly shown in FIG. 2, it will be recognized that ICE design system 200 may be connected to one or more public (e.g., the Internet) and/or private networks via one or more appropriate network connections. It will also be recognized that the software instructions comprising ICE design module 210 may also be loaded into storage 204 from a CD-ROM or other appropriate storage media via wired or wireless methods.

Moreover, those skilled in the art will appreciate that embodiments of the disclosure may be practiced with a variety of computer-system configurations, including handheld devices, multiprocessor systems, microprocessor-based or programmable-consumer electronics, minicomputers, mainframe computers, and the like. Any number of computer-systems and computer networks are acceptable for use with the present disclosure. Embodiments of the disclosure may be practiced in distributed-computing environments where tasks are performed by remote-processing devices that are linked through a communications network. In a distributed-computing environment, program modules may be located in both local and remote computer-storage media including memory storage devices. The present disclosure may therefore, be implemented in connection with various hardware, software or a combination thereof in a computer system or other processing system.

Figure 3:
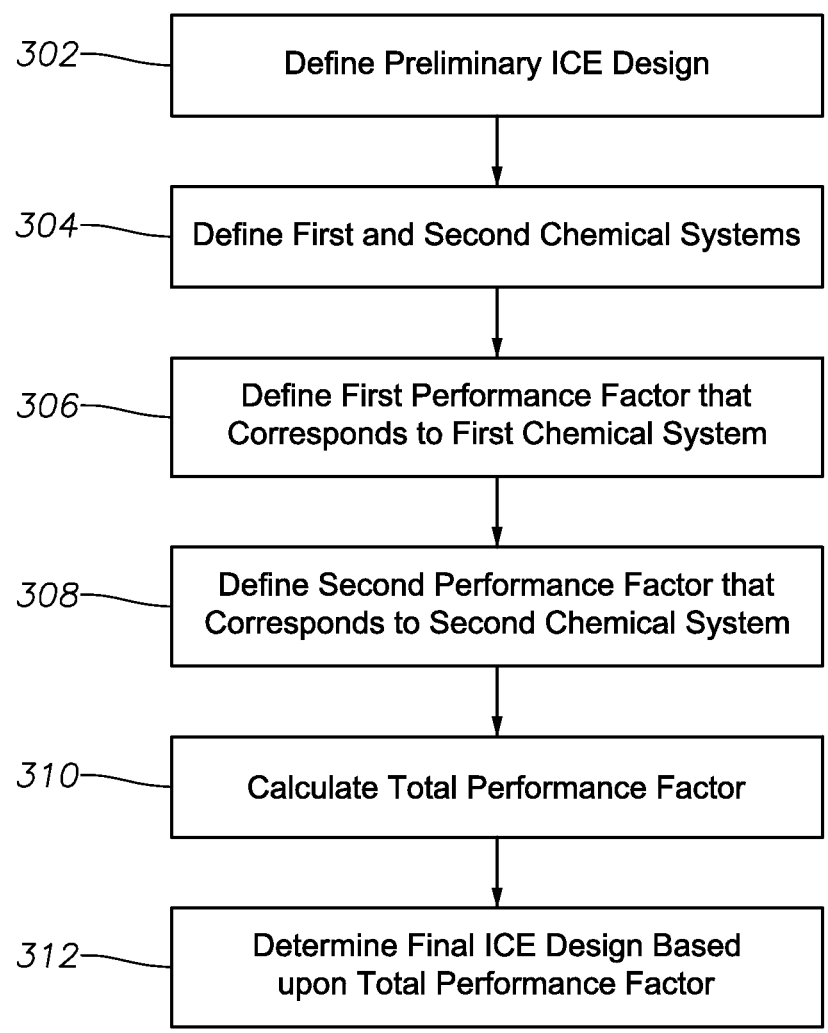
FIG. 3 is a flow chart detailing steps in a design method in accordance to an illustrative method of the present disclosure.

Referring to FIG. 3, an illustrative method 300 for designing an ICE of the present disclosure will now be described. At block 302, ICE design system 200 detects definition/entry of a preliminary ICE design and related characteristics via a user interface comprising display 208 and one or more I/O devices 206. This preliminary ICE design will form the basis of the subsequent design process. Software instructions necessary to implement and display a graphical user interface are executed by processor 202 as would be understood by those ordinarily skilled in the art having the benefit of this disclosure. In this illustrative method, the ICE-related characteristics that may be entered include, for example, number of candidate layers, materials, optical system components, calibration sample spectra or target characteristic. In one embodiment, the number of layers for a specific preliminary ICE design is inputted as a range of, for example, 6-15 layers. In another embodiment, the number of candidate layers may be inputted as a fixed number of layers. Nevertheless, all ICE-related characteristics, except for layer thicknesses, are pre-defined by the user and inputted at block 302. In an alternative embodiment, however, the ICE related characteristics may be retrieved locally from the memory of ICE design system 200 or from a remote location or database, as would be understood by those ordinarily skilled in the art having the benefit of this disclosure.

At block 304, a first and second independent chemical system is defined, each having its own calibration spectra data set. Although only two chemical systems are described in method 300, note that alternative methods may utilized three or more chemical systems as the basis for the design process. As mentioned, each chemical system has one or more components. The components are a spectral data set representing a target characteristic and interferents associated with the chemical system. Thus, the components of the first chemical system has a first characteristic and first interferent(s) associated therewith, while the second chemical system components also include a second characteristic and second interferent(s) associated therewith. The first and second characteristics and/or interferents may be the same or different, as will be described in more detail below. For example, the characteristic may be methane, with the interferents being oil or drilling fluid. The chemical systems may be defined in a variety of ways, such as, for example, through manual entry via computerized input devices or retrieved from a database having data about their properties known a priori.

At block 306, processor 202, via ICE design module 210, then determines a first performance factor of the preliminary ICE design that corresponds to the first chemical system. At block 308, processor 202 in like manner then determines a second performance factor of the preliminary ICE design that corresponds to the second chemical system. Here, the regression vector of the preliminary ICE design is applied to the calibration spectra data set of the first and second chemical systems, each calibration spectra data set having its own gain and offset values. Thus, the predictability of the single ICE design (i.e., preliminary ICE design) is applied to each calibration set independently to produce the first and second performance factors. In one illustrative embodiment, the performance factors are the SECs corresponding to the first and second chemical systems. Alternatively, however, the performance factors may be represented as the SEP, sensitivity, S/N, or % transmission.

At block 310, processor 202 then calculates a total performance factor. In a first example, the total performance factor is calculated by summing the SEC values which correspond to the first performance factor (first SEC) and the second performance factor (second SEC). The summing of the first SEC and second SEC then results in a total SEC. Thereafter, at block 312, processor 202 then determines a final ICE design based upon the total performance factor. In this example using SEC, processor 202 minimizes the total SEC, using an error minimization function, by adjusting the thicknesses of the ICE layers in the design. The resulting optimized design in the final ICE design which is output by the system.

Using the foregoing generalized method, an ICE is fabricated which is predictive for different chemical systems. For example, a single ICE fabricated according to the final ICE design may be utilized to predict a single characteristic, e.g. methane, in different types of interferents (e.g., light and heavy oil). In another example, the fabricated ICE may be utilized to measure a single characteristic, e.g. methane, in a single oil, but in different concentration ranges. This is especially useful when the components may not have a single linear response over the entire concentration range. Another example of this technique would be in the case in which the characteristic/analyte of the two different data sets are not the same; for example, the characteristic could be methane in oil and ethane in biodiesel. Accordingly, by this method, a single ICE is designed and fabricated that is predictive for different chemical systems. This can reduce the number of ICEs needed in a given application, or require fewer ICEs to be installed in a single optical computing device that can then be used for measuring different characteristics, each of which will have its own calibration spectra data set.

Figure 4:
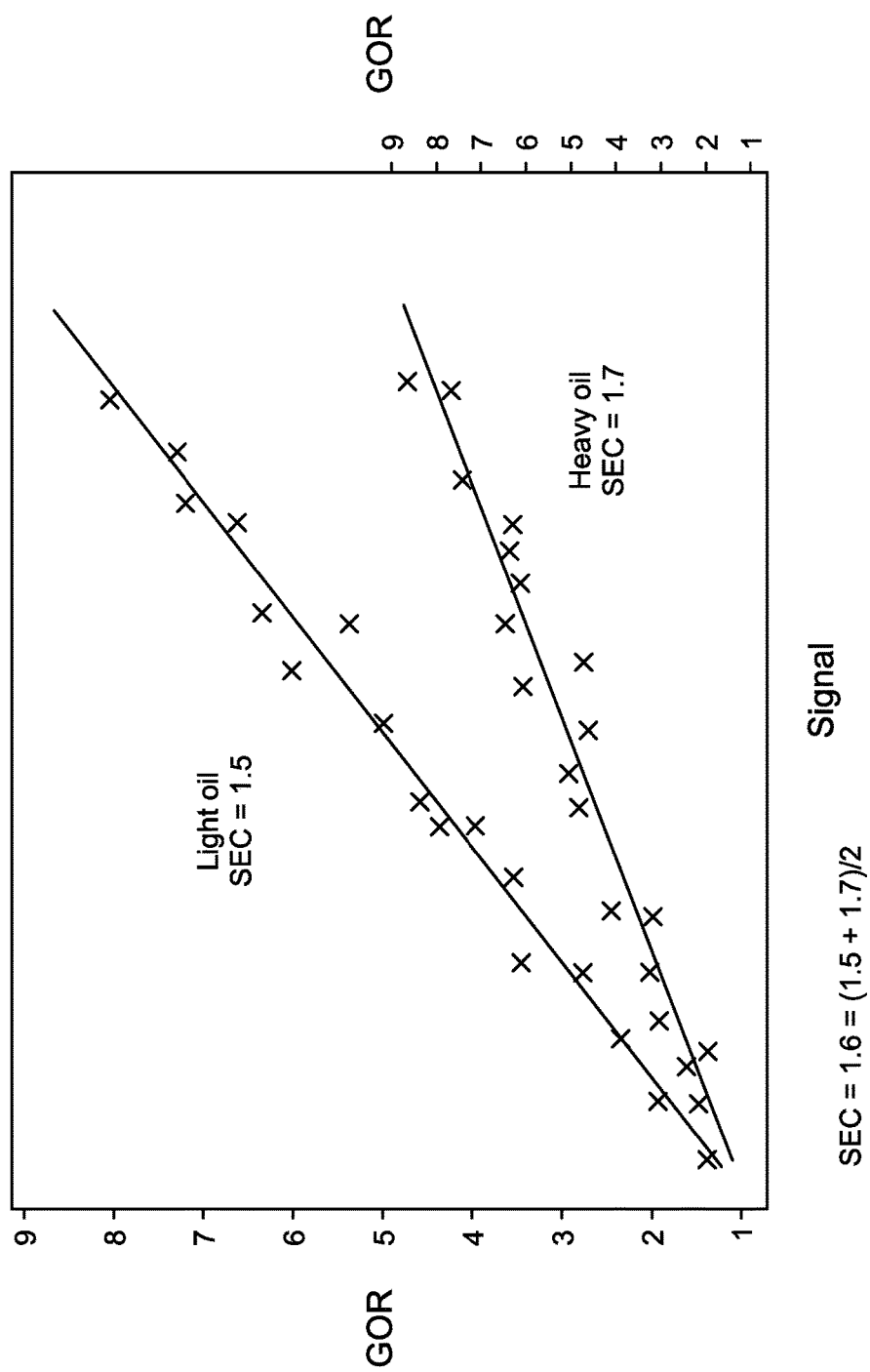
FIG. 4 is a graph useful to explain how a single ICE design may predict gas/oil ratio in two dissimilar oils, according to an illustrative embodiment of the present disclosure.

FIG. 4 is a graph useful to further illustrate method 300. An example of how a single ICE design could predict gas/oil ratio ("GOR") in two dissimilar oils is plotted in FIG. 4. The plotted preliminary ICE design is predictive for both heavy and light oils, but not both at the same time with the same calibration spectra data set. As shown, the SEC for the light oil is 1.5, while the SEC for the heavy oil is 1.7. The "x" are representative of individual samples within each calibration data set, with the SEC being represented by the straight lines through the data points. Rather than design two ICEs, embodiments of the present disclosure designs an ICE that is predictive for both, but does not necessarily have the same calibration spectra data set. Therefore, as described above, the two separate performance factors (e.g., first and second SECs) are determined, and the average predictability is minimized to thereby determine the final ICE design.

The average predictability may be minimized in a number of ways. For example, with reference to FIG. 4, simply taking an average between the two different oil types would result in a final SEC that is too high. However, through use of the methods of the present disclosure, a final ICE design is determined which is optimal for these two different sets of data, thus resulting in two calibrations which both have low SECs. Still referring to FIG. 4, instead of minimizing the design with respect to total SEC, here the minimization is accomplished with an average SEC (as shown in the Equation below the graph). Alternatively, however, this can be expressed as a weighted average of the SECs (where a factor of 0.5 is applied to each SEC and then added together for the total SEC).

In other illustrative design methods, other factors can also be included the ICE design. For example, density of the samples in the calibration set can be included in the ICE design equations (for example, by using the density component as a multiplier for the gain) if density is known to have had a direct influence on the slopes as described. In this way, ICE design system 200 may design ICEs that take into account other factors, such as density, that can be measured separately but used to improve the ICE in the design phase if they were included appropriately into the ICE design equations. For example, rather than using:

$$\text{characteristic} = (S*G) + O \qquad \text{Eq.(1)},$$

where ICE_signal is S, gain is G and offset is O, the following may be utilized:

$$\text{characteristic} = (S*G*d) + O \qquad \text{Eq.(2)}.$$

If a single gain and offset cannot accommodate light and heavy oils, another alternative approach is to include density (d) as a multiplicative correction, as shown in Equation 2.

In yet other methods, other measurable parameters may also be added into the ICE design equations in other methods, as defined by:

$$\text{characteristic} = (S*G1*d) + O + (f*G2) \qquad \text{Eq.(3)},$$

where f is a scattering component of the samples in the calibration set and G2 is a fitting parameter that would be minimized for in the design process. Generally, any physically measurable parameters can be included in the ICE minimization equation and a number optimized so as to weight the effect of the characteristic.

In yet other methods, non-linearity effects, like scattering, could also be included as a scattering component, for example:

$$\text{characteristic} = (S*G3*d)^2 + (S*G1*d) + (f*g2) + O \qquad \text{Eq.(4)},$$

where G3 is another optimization parameter.

In alternate applications, the method described above may be applied to any optical system or component in which a single system calibration can be used for multiple characteristics/analytes. Moreover, a mathematical regression vector for a spectrometer could also be defined using the method.

Figure 5:
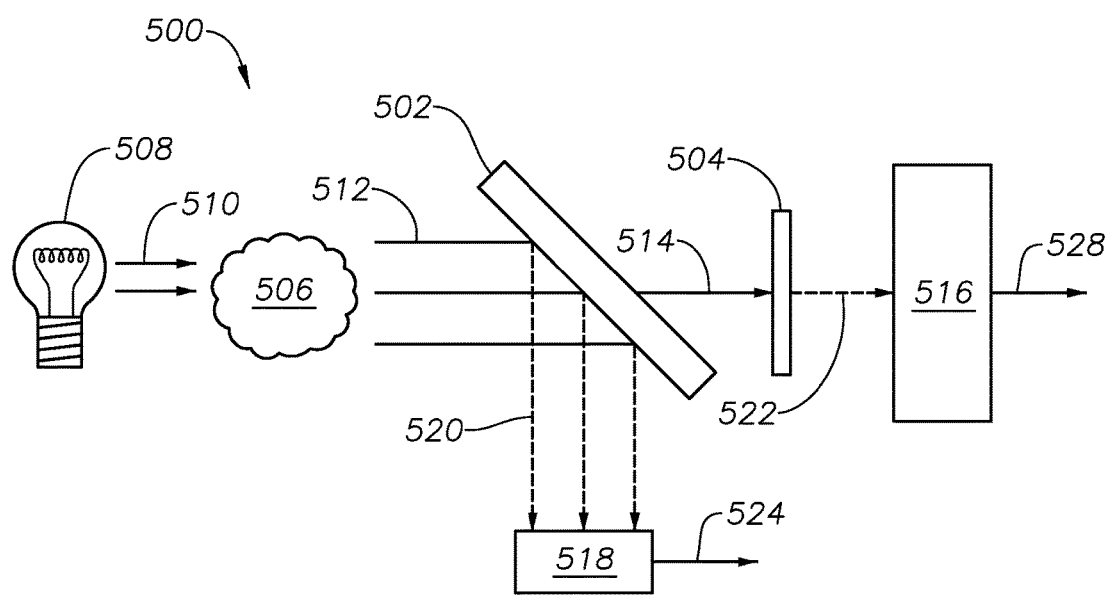
FIG. 5 is a block diagram of an optical computing device utilizing a multi-characteristic ICE, according to illustrative embodiments of the present disclosure.

FIG. 5 is a block diagram of an illustrative architecture of an optical computing device 500 utilizing an ICE designed using the illustrative methods described herein. An electromagnetic radiation source 508 may be configured to emit or otherwise generate electromagnetic radiation 510. As understood in the art, electromagnetic radiation source 508 may be any device capable of emitting or generating electromagnetic radiation. For example, electromagnetic radiation source 508 may be a light bulb, light emitting device, laser, blackbody, photonic crystal, or X-Ray source, natural luminescence, etc. In one embodiment, electromagnetic radiation 510 may be configured to optically interact with the sample 506 to thereby generate sample-interacted light 512. Sample 506 may be any desired sample, such as, for example, a fluid (liquid or gas), solid substance or material such as, for example, hydrocarbons or food products. While FIG. 5 shows electromagnetic radiation 510 as passing through or incident upon the sample 506 to produce sample-interacted light 512 (i.e., transmission or fluorescent mode), it is also contemplated herein to reflect electromagnetic radiation 510 off of the sample 506 (i.e., reflectance mode), such as in the case of a sample 506 that is translucent, opaque, or solid, and equally generate the sample-interacted light 512.

After being illuminated with electromagnetic radiation 510, sample 506 containing an analyte of interest (a characteristic of the sample) produces an output of electromagnetic radiation (sample-interacted light 512, for example). As previously described, sample-interacted light 512 also contains spectral information of the sample used to determine one or more characteristics of sample 506. Although not specifically shown, one or more spectral elements may be employed in optical computing device 500 in order to restrict the optical wavelengths and/or bandwidths of the system and, thereby, eliminate unwanted electromagnetic radiation existing in wavelength regions that have no importance. As will be understood by those ordinarily skilled in the art having the benefit of this disclosure, such spectral elements can be located anywhere along the optical train, but are typically employed directly after the light source which provides the initial electromagnetic radiation.

Although not shown, optical computing device 500 may be coupled to a remote power supply, while in other embodiments optical computing device 500 comprises an on-board battery. Optical computing device 500 may also comprise a signal processor (not shown), communications module (not shown) and other circuitry necessary to achieve the objectives of the present disclosure, as will be understood by those ordinarily skilled in the art having the benefit of this disclosure. It will also be recognized that the software instructions necessary to carry out the objectives of the present disclosure may be stored within storage located on optical computing device 500 or loaded into that storage from a CD-ROM or other appropriate storage media via wired or wireless methods.

Alternatively, however, the processor may be located remotely from optical computing device 500. In such embodiments, a communications link provides a medium of communication between the processor and optical computing device 500. The communications link may be a wired link, such as, for example, a fiber optic cable. Alternatively, however, the link may be a wireless link. In certain illustrative embodiments, the signal processor controls operation of optical computing device 500. Optical computing device 500 may also include a transmitter and receiver (transceiver, for example) (not shown) that allows bi-directional communication over a communications link in real-time. In certain illustrative embodiments, optical computing device 500 will transmit all or a portion of the sample characteristic data to a remote processor for further analysis. However, in other embodiments, such analysis is completely handled by optical computing device 500 and the resulting data is then transmitted remotely for storage or subsequent analysis. In either embodiment, the processor handling the computations may, for example, analyze the characteristic data, or perform simulations based upon the characteristic data, as will be readily understood by those ordinarily skilled in the art having the benefit of this disclosure.

Still referring to the illustrative embodiment of FIG. 5, beam splitter 502 is employed to split sample-interacted light 512 into a transmitted electromagnetic radiation 514 and a reflected electromagnetic radiation 520. Transmitted electromagnetic radiation 514 is then directed to one or more optical elements 504. Optical element 504 may be an ICE as described herein to determine multiple characteristics of sample 506. The ICE is designed to correspond with a plurality of chemical systems or may be designed to approximate or mimic the regression vector of the plurality of chemical systems, as would be understood by those ordinarily skilled in the art having the benefit of this disclosure. As previously discussed, the chemical systems may comprise, for example, a single characteristic in different fluids, a single characteristic having differing ranges in the different fluids, or different characteristics. Additionally, in an alternative embodiment, optical element 504 may function as both a beam splitter and multivariate computational processor, as will be understood by those same ordinarily skilled persons.

Nevertheless, transmitted electromagnetic radiation 514 then optically interacts with optical element 504 to produce optically interacted light 522. In this embodiment, optically interacted light 522, which is related to at least one characteristic of sample 506, is conveyed to detector 516 for analysis and quantification. As previously described, the characteristic reflected in optically interacted light 522 may be a single characteristic or multiple characteristics of sample 506 (even in the event that sample 506 comprises different fluids). Moreover, optically interacted light 522 may simultaneously reflect multiple characteristics or a first and second optically interacted light may correspond with the first and second characteristic, respectively, the second characteristic being different from the first characteristic. Alternatively, for example, the first and second optically interacted lights may correspond to a first and second centration range of the characteristic, wherein the first concentration range is different from the second concentration range. In yet another embodiment, sample 506 may comprise two different fluids (e.g., first and second fluids). In such cases, the first and second optically interacted lights may correspond to the same characteristics present in both the first and second fluids.

Nevertheless, detector 516 may be any device capable of detecting electromagnetic radiation, and may be generally characterized as an optical transducer. For example, detector 516 may be, but is not limited to, a thermal detector such as a thermopile or photoacoustic detector, a semiconductor detector, a piezo-electric detector, charge coupled device detector, video or array detector, split detector, photon detector (such as a photomultiplier tube), photodiodes, local or distributed optical fibers, and/or combinations thereof, or the like, or other detectors known to those ordinarily skilled in the art. Detector 516 is further configured to produce an output signal 528 in the form of a voltage that corresponds to the characteristic of the sample 506. In at least one embodiment, output signal 528 produced by detector 516 and the characteristic concentration of the sample 506 may be directly proportional. In other embodiments, the relationship may be a polynomial function, an exponential function, and/or a logarithmic function.

Optical computing device 500 includes a second detector 518 arranged to receive and detect reflected electromagnetic radiation and output a normalizing signal 524. As understood in the art, reflected electromagnetic radiation 520 may include a variety of radiating deviations stemming from electromagnetic radiation source 508 such as, for example, intensity fluctuations in the electromagnetic radiation, interferent fluctuations (for example, dust or other interferents passing in front of the electromagnetic radiation source), combinations thereof, or the like. Thus, second detector 518 detects such radiating deviations as well. In an alternative embodiment, second detector 518 may be arranged to receive a portion of the sample-interacted light 512 instead of reflected electromagnetic radiation 520, and thereby compensate for electromagnetic radiating deviations stemming from the electromagnetic radiation source 508. In yet other embodiments, second detector 518 may be arranged to receive a portion of electromagnetic radiation 510 instead of reflected electromagnetic radiation 520, and thereby likewise compensate for electromagnetic radiating deviations stemming from the electromagnetic radiation source 508. Those ordinarily skilled in the art having the benefit of this disclosure will realize there are a variety of design alterations which may be utilized in conjunction with embodiments of the present disclosure.

Although not shown in FIG. 5, in certain illustrative embodiments, detector 516 and second detector 518 may be communicably coupled to a signal processor (not shown) on-board optical computing device 500 such that normalizing signal 524 indicative of electromagnetic radiating deviations may be provided or otherwise conveyed thereto. The signal processor may then be configured to computationally combine normalizing signal 524 with output signal 528 to provide a more accurate determination of the one or more characteristics of sample 506. However, in other embodiments that utilized only one detector, the signal processor would be coupled to the one detector. Nevertheless, in the embodiment of FIG. 5, for example, the signal processor computationally combines normalizing signal 524 with output signal 528 via principal component analysis techniques such as, for example, standard partial least squares which are available in most statistical analysis software packages (for example, XL Stat for MICROSOFT® EXCEL®; the UNSCRAMBLER® from CAMO Software and MATLAB® from MATHWORKS®), as will be understood by those ordinarily skilled in the art having the benefit of this disclosure. Thereafter, the resulting data is then transmitted to the processor for further operations.

Embodiments described herein further relate to any one or more of the following paragraphs:

1. A method for designing an Integrated Computational Element ("ICE"), comprising defining a preliminary ICE design; defining a first chemical system having one or more components; defining a second chemical system having one or more components; determining a first performance factor of the preliminary ICE design which corresponds to the first chemical system; determining a second performance factor of the preliminary ICE design which corresponds to the second chemical system; summing the first and second performance factors to produce a total performance factor; and determining a final ICE design based upon the total performance factor.

2. A method as described in paragraph 1, wherein the first performance factor is a first standard error of calibration ("SEC"); the second performance factor is a second SEC; the total performance factor is a total SEC; and determining the final ICE design comprises adjusting thicknesses of ICE layers to thereby minimize the total SEC.

3. A method as described in paragraphs 1 or 2, wherein the components of the first chemical system are a set of spectral data representing a first characteristic and first interferents associated with the first chemical system; and the components of the second chemical system are a set of spectral data representing the first characteristic and second interferents associated with the second chemical system, the second interferents being different from the first interferents.

4. A method as described in any of paragraphs 1-3, wherein the components of the first chemical system are a set of spectral data representing a first characteristic and interferents associated with the first chemical system; and the components of the second chemical system are a set of spectral data representing a second characteristic and interferents associated with the second chemical system, the second characteristic being different from the first characteristic.

5. A method as defined in any of paragraphs 1-4, wherein determining the first performance factor comprises: defining a first calibration data set for the first chemical system; and applying a regression vector of the preliminary ICE design to the first data set; and determining the second performance factor comprises: defining a second calibration data set for the second chemical system; and applying the regression vector of the preliminary ICE design to the second data set.

6. A method as defined in any of paragraphs 1-5, wherein the first calibration data set has a first gain and offset value; and the second calibration data set has a second gain and offset value.

7. A method as defined in any of paragraphs 1-6, wherein the first and second calibration data sets comprise a density component.

8. A method as defined in any of paragraphs 1-7, wherein the first and second calibration data sets comprise a scattering component.

9. A method as defined in any of paragraphs 1-8, wherein the final ICE design corresponds to a single characteristic in different chemical systems.

10. A method as defined in any of paragraphs 1-9, wherein the single characteristic is methane; and the different chemical systems comprise: a light oil and a heavy oil; or an oil and a gas.

11. A method as defined in any of paragraphs 1-10, wherein the final ICE design corresponds to different characteristics.

12. A method for designing an Integrated Computational Element ("ICE"), comprising defining a plurality of chemical systems that each represent one or more components; and determining a single ICE design that corresponds to the plurality of chemical systems.

13. A method as defined in paragraph 12, wherein the one or more components of each chemical system represent at least one of a characteristic or spectral interferent.

14. A method as defined in paragraphs 12 or 13, wherein determining the single ICE design comprises defining calibration data sets representing the chemical systems; applying a regression vector to the calibration data sets to thereby determine a performance factor; and determining the single ICE design which minimizes the performance factor.

15. A method as defined in any of paragraphs 12-14, wherein the calibration data sets have different gain or offset values.

16. An Integrated Computational Element ("ICE") fabricated using any of the methods defined in any of paragraphs 1-15.

17. An Integrated Computational Element ("ICE") designed to correspond to a plurality of chemical systems.

18. An ICE as defined in paragraph 17, wherein the chemical systems comprise: a single characteristic in different fluids; a single characteristic having differing concentration ranges in a single fluid; or different characteristics.

19. An optical computing device, comprising an electromagnetic radiation that optically interacts with a fluid sample to produce sample-interacted light; at least one Integrated Computational Element ("ICE") configured to correspond to a plurality of chemical systems, the at least one ICE being positioned to optically interact with the sample-interacted light to produce optically-interacted light that corresponds to at least one characteristic within the fluid sample; and an optical transducer positioned to receive the optically-interacted light and thereby generate a signal corresponding to the at least one characteristic of the fluid sample.

20. A device as defined in paragraph 19, wherein the chemical systems comprise a single characteristic in different fluids; a single characteristic having differing ranges in the different fluids; or different characteristics.

21. A device as defined in paragraphs 19 or 20, wherein the at least one characteristic comprises two different characteristics; or the at least one characteristic comprises a single characteristic, and the fluid sample comprises different fluids.

22. An optical computing method, comprising optically interacting electromagnetic radiation with a fluid sample to produce sample-interacted light; optically interacting the sample-interacted light with an Integrated Computational Element ("ICE") to thereby generate optically-interacted light with corresponds to at least one characteristic of the fluid sample, the ICE being configured to correspond to a plurality of chemical systems; utilizing an optical transducer to generate a signal that corresponds to the at least one characteristic; and determining the at least one characteristic using the signal.

23. A method as defined in paragraph 22, wherein generating the optically-interacted light comprises generating a first optically-interacted light which corresponds to a first characteristic of the fluid sample; and generating a second optically-interacted light which corresponds to a second characteristic of the fluid sample, the second characteristic being different from the first characteristic.

24. A method as defined in paragraphs 22 or 23, wherein generating the optically-interacted light comprises generating a first optically-interacted light which corresponds to a first concentration range of the characteristic; and generating a second optically-interacted light which corresponds to a second concentration range of the characteristic, wherein the first concentration range is different from the second concentration range.

25. A method as defined in any of paragraphs 22-24, wherein the fluid sample comprises a first fluid and a second fluid different from the first fluid; and generating the optically-interacted light comprises: generating a first optically-interacted light which corresponds to the characteristic present in the first fluid; and generating a second optically-interacted light which corresponds to the characteristic present in the second fluid.

26. A system comprising processing circuitry to implement any of the methods of paragraphs 1-25.

Moreover, the methodologies described herein may be embodied within a system comprising processing circuitry to implement any of the methods, or a in a computer-program product comprising instructions which, when executed by at least one processor, causes the processor to perform any of the methods described herein.

Although various embodiments and methodologies have been shown and described, the disclosure is not limited to such embodiments and methodologies and will be understood to include all modifications and variations as would be apparent to one skilled in the art. Therefore, it should be understood that the disclosure is not intended to be limited to the particular forms disclosed. Rather, the intention is to cover all modifications, equivalents and alternatives falling within the spirit and scope of the disclosure as defined by the appended claims.

What is claimed is:

1. A method for designing an Integrated Computational Element ("ICE"), comprising:
defining a preliminary ICE design;
defining a first chemical system having one or more components;
defining a second chemical system having one or more components;
determining a first performance factor of the preliminary ICE design which corresponds to the first chemical system;
determining a second performance factor of the preliminary ICE design which corresponds to the second chemical system;
summing the first and second performance factors to produce a total performance factor;
determining a final ICE design based upon the total performance factor; and
fabricating an ICE according to the final ICE design.

2. A method as described in claim 1, wherein:
the first performance factor is a first standard error of calibration ("SEC");
the second performance factor is a second SEC;
the total performance factor is a total SEC; and
determining the final ICE design comprises adjusting thicknesses of ICE layers to thereby minimize the total SEC.

3. A method as described in claim 1, wherein:
the components of the first chemical system are a set of spectral data representing a first characteristic and first interferents associated with the first chemical system; and
the components of the second chemical system are a set of spectral data representing the first characteristic and second interferents associated with the second chemical system, the second interferents being different from the first interferents.

4. A method as described in claim 1, wherein:
the components of the first chemical system are a set of spectral data representing a first characteristic and interferents associated with the first chemical system; and
the components of the second chemical system are a set of spectral data representing a second characteristic and interferents associated with the second chemical system, the second characteristic being different from the first characteristic.

5. A method as defined in claim 1, wherein:
determining the first performance factor comprises:
defining a first calibration data set for the first chemical system; and
applying a regression vector of the preliminary ICE design to the first data set; and
determining the second performance factor comprises:
defining a second calibration data set for the second chemical system; and
applying the regression vector of the preliminary ICE design to the second data set.

6. A method as defined in claim 5, wherein:
the first calibration data set has a first gain and offset value; and
the second calibration data set has a second gain and offset value.

7. A method as defined in claim 5, wherein the first and second calibration data sets comprise a density component.

8. A method as defined in claim 5, wherein the first and second calibration data sets comprise a scattering component.

9. A method as defined in claim 1, wherein the final ICE design corresponds to a single characteristic in different chemical systems.

10. A method as defined in claim 9, wherein:
the single characteristic is methane; and the different chemical systems comprise:
a light oil and a heavy oil; or
an oil and a gas.

11. A method as defined in claim 1, wherein the final ICE design corresponds to different characteristics.

12. An Integrated Computational Element ("ICE") fabricated using the method defined in claim 1.

13. A system comprising processing circuitry to implement the method of claim 1.

14. A method for designing an Integrated Computational Element ("ICE"), comprising:
defining a plurality of chemical systems that each represent one or more components;
determining a single ICE design that corresponds to the plurality of chemical systems; and
fabricating an ICE according to the single ICE design.

15. A method as defined in claim 14, wherein the one or more components of each chemical system represent at least one of a characteristic or spectral interferent.

16. A method as defined in claim 14, wherein determining the single ICE design comprises:
defining calibration data sets representing the chemical systems;
applying a regression vector to the calibration data sets to thereby determine a performance factor; and
determining the single ICE design which minimizes the performance factor.

17. A method as defined in claim 16, wherein the calibration data sets have different gain or offset values.

18. An Integrated Computational Element ("ICE") which approximates a regression vector of a plurality of chemical systems.

19. An ICE as defined in claim 18, wherein the chemical systems comprise:
a single characteristic in different fluids;
a single characteristic having differing concentration ranges in a single fluid; or
different characteristics.

20. An optical computing device, comprising:
an electromagnetic radiation source which produces electromagnetic radiation that optically interacts with a fluid sample to produce sample-interacted light;
at least one Integrated Computational Element ("ICE") that approximates a regression vector of a plurality of chemical systems, the at least one ICE being positioned to optically interact with the sample-interacted light to produce optically-interacted light that corresponds to at least one characteristic within the fluid sample; and
an optical transducer positioned to receive the optically-interacted light and thereby generate a signal corresponding to the at least one characteristic of the fluid sample.

21. A device as defined in claim 20, wherein the chemical systems comprise:
a single characteristic in different fluids;
a single characteristic having differing ranges in the different fluids; or
different characteristics.

22. A device as defined in claim 20, wherein:
the at least one characteristic comprises two different characteristics; or
the at least one characteristic comprises a single characteristic, and the fluid sample comprises different fluids.

23. An optical computing method, comprising:
optically interacting electromagnetic radiation with a fluid sample to produce sample-interacted light;
optically interacting the sample-interacted light with an Integrated Computational Element ("ICE") to thereby generate optically-interacted light which corresponds to at least one characteristic of the fluid sample, wherein the ICE approximates a regression vector of a plurality of chemical systems;
utilizing an optical transducer to generate a signal that corresponds to the at least one characteristic; and
determining the at least one characteristic using the signal.

24. A method as defined in claim 23, wherein generating the optically-interacted light comprises:
generating a first optically-interacted light which corresponds to a first characteristic of the fluid sample; and
generating a second optically-interacted light which corresponds to a second characteristic of the fluid sample, the second characteristic being different from the first characteristic.

25. A method as defined in claim 23, wherein generating the optically-interacted light comprises:
generating a first optically-interacted light which corresponds to a first concentration range of the characteristic; and
generating a second optically-interacted light which corresponds to a second concentration range of the characteristic, wherein the first concentration range is different from the second concentration range.

26. A method as defined in claim 23, wherein:
the fluid sample comprises a first fluid and a second fluid different from the first fluid; and
generating the optically-interacted light comprises:
generating a first optically-interacted light which corresponds to the characteristic present in the first fluid; and
generating a second optically-interacted light which corresponds to the characteristic present in the second fluid.

* * * * *